(12) United States Patent
Kim

(10) Patent No.: US 11,967,082 B2
(45) Date of Patent: Apr. 23, 2024

(54) METHOD AND DEVICE FOR CORRECTING BRAIN IMAGE BY USING BRAIN STRUCTURE

(71) Applicant: NEUROPHET INC., Seoul (KR)

(72) Inventor: Dong Hyeon Kim, Seoul (KR)

(73) Assignee: NEUROPHET INC., Seoul (KR)

( * ) Notice: Subject to any disclaimer, the term of this patent is extended or adjusted under 35 U.S.C. 154(b) by 348 days.

(21) Appl. No.: 17/403,959

(22) Filed: Aug. 17, 2021

(65) Prior Publication Data

US 2021/0374966 A1 Dec. 2, 2021

Related U.S. Application Data

(63) Continuation of application No. PCT/KR2020/003017, filed on Mar. 3, 2020.

(30) Foreign Application Priority Data

Mar. 5, 2019 (KR) .................. 10-2019-0025001

(51) Int. Cl.
  *G06T 7/11* (2017.01)
  *G06T 7/187* (2017.01)
  *G06T 17/00* (2006.01)

(52) U.S. Cl.
  CPC ............... *G06T 7/11* (2017.01); *G06T 7/187* (2017.01); *G06T 17/00* (2013.01); *G06T 2207/20081* (2013.01); *G06T 2207/20084* (2013.01); *G06T 2207/30016* (2013.01)

(58) Field of Classification Search
  CPC . G06T 7/11; G06T 7/187; G06T 17/00; G06T 2207/20081; G06T 2207/20084; G06T 2207/30016; G06T 2210/41; G06T 5/001; G06T 17/20
  See application file for complete search history.

(56) References Cited

U.S. PATENT DOCUMENTS

| 2011/0304332 A1* | 12/2011 | Mahfouz ................ A61F 2/389 324/309 |
| 2012/0155733 A1* | 6/2012 | Wagenknecht ...... G06T 11/005 382/131 |
| 2015/0038812 A1* | 2/2015 | Ayaz .................. A61B 5/14553 600/328 |

(Continued)

FOREIGN PATENT DOCUMENTS

| JP | 2012-531229 A | 12/2012 |
| JP | 2019-005557 A | 1/2019 |

(Continued)

OTHER PUBLICATIONS

International Search Report issued in PCT/KR2020/003017; mailed Jun. 12, 2020.

*Primary Examiner* — Ming Y Hon
(74) *Attorney, Agent, or Firm* — Studebaker & Brackett PC

(57) ABSTRACT

Provided is a method, performed by a computer, for correcting a brain image by using a brain structure. The method comprises: a step for obtaining a head image including the brain of a subject; a step for dividing the head image into a plurality of regions on the basis of the brain structure; and a step for performing a correction on the plurality of regions by using a layer arrangement condition of the brain.

11 Claims, 12 Drawing Sheets

(56) References Cited

U.S. PATENT DOCUMENTS

| | | | | |
|---|---|---|---|---|
| 2015/0076920 A1* | 3/2015 | Zargham | ................ | H02J 50/10 |
| | | | | 307/104 |
| 2016/0038770 A1* | 2/2016 | Tyler | ....................... | A61N 7/00 |
| | | | | 601/2 |
| 2016/0155364 A1* | 6/2016 | Piron | ..................... | G01R 33/58 |
| | | | | 434/270 |
| 2016/0360966 A1* | 12/2016 | Ishii | ...................... | G16C 10/00 |
| 2019/0057623 A1* | 2/2019 | Magsood | .............. | B29C 39/003 |
| 2019/0059732 A1* | 2/2019 | Kim | .................... | A61B 5/0042 |
| 2019/0380780 A1* | 12/2019 | Sela | ...................... | G09B 23/28 |
| 2021/0015366 A1* | 1/2021 | Agrawal | .............. | G06T 11/008 |

FOREIGN PATENT DOCUMENTS

| | | |
|---|---|---|
| KR | 10-2014-0001294 A | 1/2014 |
| KR | 10-2017-0116100 A | 10/2017 |
| KR | 10-1950815 B1 | 2/2019 |

* cited by examiner

METHOD AND DEVICE FOR CORRECTING BRAIN IMAGE BY USING BRAIN STRUCTURE

CROSS-REFERENCE TO RELATED APPLICATIONS

The present application is a continuation of International Patent Application No. PCT/KR2020/003017, filed on Mar. 3, 2020, which is based upon and claims the benefit of priority to Korean Patent Application No. 10-2019-0025001 filed on Mar. 5, 2019. The disclosures of the above-listed applications are hereby incorporated by reference herein in their entirety.

BACKGROUND

Embodiments of the present invention described herein relate to a method and a device for correcting a brain image by using a brain structure.

Electrical brain stimulation refers to allow a current to flow to electrodes attached to an inner portion or an outer portion of a head such that the current is finally applied to a brain. The electrical brain stimulation that is non-invasive treatment for a simple operation is widely used to treat various brain diseases depending on types of the stimulation and locations to which the stimulation is applied.

Also, electroencephalogram (EEG) capable of measuring electricity activity resulting from brain activity of an object is widely used in the neurology and the neuropsychiatric treatment.

The electrical brain stimulation and the electroencephalogram (EEG) that all are non-invasive test and treatment manners make the operation simple. Also, a brain image of each object to be treated is obtained for the above operation, and the treatment is made through the obtained brain image. In this case, it is important to obtain a brain image appropriate to an operation purpose. In particular, it is important to obtain a brain image in which respective brain regions are classified to coincide with a real brain structure. Accordingly, there is required a method for classifying respective brain regions through the brain image so as to coincide with the real brain structure.

SUMMARY

Embodiments of the present invention provide a method and a device for correcting a brain image by using a brain structure.

Embodiments of the present invention provide a method and a device for obtaining a brain image segmented into a plurality of brain regions coinciding with a layer arrangement condition of a brain.

Embodiments of the present invention provide a method and a device for detecting a brain region not satisfying a layer arrangement condition of a brain from a brain image and correcting the detected brain region.

Problems to be solved by the present invention are not limited to the problems mentioned above, and other problems not mentioned will be clearly understood by those skilled in the art from the following description.

According to an embodiment of the present invention, a method for correcting a brain image by using a brain structure, which is performed by a computer, includes obtaining a head image including a brain of an object, segmenting the head image into a plurality of regions based on the brain structure, and performing correction on the plurality of regions by using a layer arrangement condition of a brain.

In an embodiment of the present invention, the segmenting into the plurality of regions may include segmenting the brain in the head image into the plurality of regions by using a learning model labeling a brain based on the brain structure.

In an embodiment of the present invention, each of the plurality of regions may correspond to each of brain regions labeled through the learning model based on the brain structure.

In an embodiment of the present invention, the performing of the correction may include determining whether to coincide with the layer arrangement condition of the brain with respect to the plurality of regions, and extracting and correcting a region, which does not coincide with the layer arrangement condition of the brain, from among the plurality of regions, and the layer arrangement condition of the brain may be set based on a layer structure of a brain arranged in the order of a skin, a skull, cerebrospinal fluid, and an inner brain region.

In an embodiment of the present invention, the layer arrangement condition of the brain may include at least one of a first condition that a layer disposed outside a layer corresponding to the skin does not exist, a second condition that a layer corresponding to the cerebrospinal fluid does not contact the layer corresponding to the skin, a third condition that a layer corresponding to the inner brain region does not contact a layer corresponding to the skull or the layer corresponding to the skin, a fourth condition that a layer corresponding to a white matter in the inner brain region does not exist outside a layer corresponding to a gray matter in the inner brain region, and a fifth condition that an arrangement distribution of all layers in the layer structure of the brain is within a given range.

In an embodiment of the present invention, the extracting and correcting of the region not coinciding with the layer arrangement condition of the brain may include rearranging the region not coinciding with the layer arrangement condition of the brain so as to coincide with the layer structure of the brain arranged in the order of the skin, the skull, the cerebrospinal fluid, and the inner brain region.

In an embodiment of the present invention, the method may further include performing three-dimensional brain modeling on the object based on the head image corrected by using the layer arrangement condition of the brain.

In an embodiment of the present invention, the method may further include simulating electrical stimulation for the brain of the object based on the head image corrected by using the layer arrangement condition of the brain.

According to an embodiment of the present invention, a device includes a memory that stores one or more instructions, and a processor that executes the one or more instructions stored in the memory. The processor may execute the one or more instructions to obtain a head image including a brain of an object, to segment the head image into a plurality of regions based on the brain structure, and to perform correction on the plurality of regions by using a layer arrangement condition of a brain.

According to an embodiment of the present invention, a computer program is stored in a computer-readable recording medium so as to perform the brain image correcting method using the brain structure in combination with a computer being hardware.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
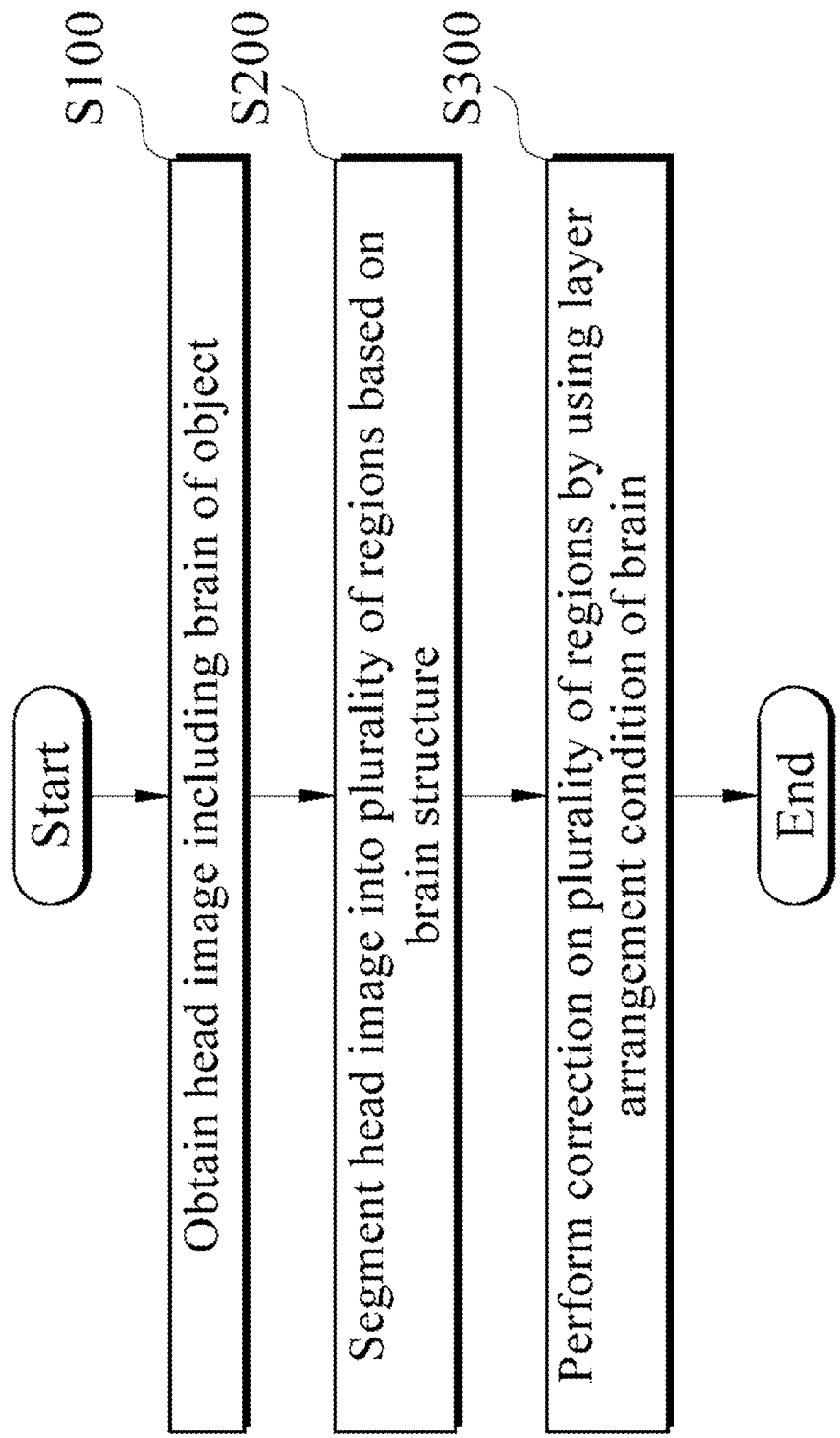
FIG. 1 is a flowchart illustrating a method for correcting a brain image by using a brain structure, according to an embodiment of the present invention.

The above and other aspects, features and advantages of the present invention will become apparent from embodiments to be described in detail in conjunction with the accompanying drawings. The present invention, however, may be embodied in various different forms, and should not be construed as being limited only to the illustrated embodiments. Rather, these embodiments are provided as examples so that the present invention will be thorough and complete, and will fully convey the scope of the present invention to those skilled in the art. The present invention may be defined by the scope of the claims.

The terms used herein are provided to describe embodiments, not intended to limit the present invention. In the specification, the singular forms include plural forms unless particularly mentioned. The terms "comprises" and/or "comprising" used herein do not exclude the presence or addition of one or more other components, in addition to the aforementioned components. The same reference numerals denote the same components throughout the specification. As used herein, the term "and/or" includes each of the associated components and all combinations of one or more of the associated components. It will be understood that, although the terms "first", "second", etc., may be used herein to describe various components, these components should not be limited by these terms. These terms are only used to distinguish one component from another component. Thus, a first component that is discussed below could be termed a second component without departing from the technical idea of the present invention.

Unless otherwise defined, all terms (including technical and scientific terms) used herein have the same meaning as commonly understood by those skilled in the art to which the present invention pertains. The terms, such as those defined in commonly used dictionaries, should not be interpreted in an idealized or overly formal sense unless expressly so defined herein.

The term "unit" or "module" used herein may refer to software or hardware such as field programmable gate array (FPGA) or application specific integrated circuit (ASIC), and the "unit" or "module" may perform some functions. However, the "unit" or "module" may be not limited to software or hardware. The "unit" or "module" may be configured to exist in an addressable storage medium or may be configured to operate one or more processors. Accordingly, as an example, "units" or "module" may include various elements such as software elements, object-oriented software elements, class elements, and task elements, processes, functions, attributes, procedures, subroutines, program code segments, drivers, firmware, microcodes, circuits, data, databases, data structures, tables, arrays, and variables. Functions provided in "units" or "modules" and components may be combined into a smaller number of "units" or "modules" and components or may be divided into additional "units" or "modules" and components.

In the specification, a "computer" includes all of various devices capable of providing results to a user by performing arithmetic processing. For example, the computer may correspond to not only a desktop personal computer (PC) or a notebook but also a smart phone, a tablet PC, a cellular phone, a personal communication service (PCS) phone, a mobile terminal of a synchronous/asynchronous International Mobile Telecommunication-2000 (IMT-2000), a palm PC, a personal digital assistant (PDA), and the like. Besides, when a head-mounted display (HMD) device includes a computing function, the HMD device may be a computer. Furthermore, the computer may correspond to a server that receives a request from a client and processes information.

Hereinafter, an embodiment of the present invention will be described in detail with reference to the accompanying drawings.

FIG. 1 is a flowchart illustrating a method for correcting a brain image by using a brain structure, according to an embodiment of the present invention.

The method of FIG. 1 is described as being performed by a computer for convenience of explanation, but the subject of performing each step is not limited to a specific device and may be used in the sense of encompassing devices capable of performing computing processing. That is, in this embodiment, the computer may refer to a device capable of performing the brain image correcting method using the brain structure.

Referring to FIG. 1, according to an embodiment of the present invention, the brain image correcting method using the brain structure may include steps of obtaining a head image including a brain of an object (S100), segmenting the head image into a plurality of regions based on the brain structure (S200), and performing correction on the plurality of regions by using a layer arrangement condition of a brain (S300). Below, each step will be described in detail.

A computer may obtain the head image including the brain of the object (S100).

Here, the object may include a person, an animal, a part of a person, or a part of an animal.

The head image refers to a medical image obtained by photographing the head including the brain of the object. For example, the head image may include a computed tomography (CT) image, a magnetic resonance imaging (MRI) image, a positron emission tomography (PET) images, and the like, which are photographed by a medical imaging device.

Also, the head image may be a medical image that is photographed to include a skull and a scalp (i.e., skin) of the object, as well as the brain of the object.

The computer may segment the head image of the object into a plurality of regions based on the brain structure (S200).

In an embodiment, the computer may segment the head image of the object for each brain region, based on the brain structure.

Here, the brain structure may be formed of a layer structure, for example, may include a scalp (i.e., skin), a skull, cerebrospinal fluid, and an inner brain region. Also, the inner brain region may include the cerebrum, the cerebellum, and the ventricle. The cerebrum and the cerebellum may be formed of a layer structure in which the cerebrum and cerebellum are more subdivided into a gray matter and a white matter.

That is, the computer may segment the head image of the object into the plurality of regions corresponding to the layer structure of the brain, based on the scalp, the skull, the cerebrospinal fluid, and the inner brain regions (i.e., the gray matter/white matter of the cerebrum, the gray matter/white matter of the cerebellum, and the ventricle).

Here, the layer structure of the brain is described as being composed of the scalp, the skull, the cerebrospinal fluid, and the inner brain region (i.e., the gray matter/white matter of the cerebrum, the gray matter/white matter of the cerebellum, the ventricle). However, the above layer structure is only an example, and the present invention is not limited thereto. According to an embodiment, the structure of the brain may be classified in any other way, and kinds of brain regions may vary depending on the way to classify.

Also, the computer may segment the head image of the object into the plurality of regions through learning. In an embodiment, the computer may segment the brain included in the head image of the object into the plurality of regions by using a learning model labeling a brain for each region based on the brain structure. Here, the learning model may be created through the learning using the deep learning.

For example, the computer may obtain medical images, which are generated by photographing the head including the brain, from a plurality of objects and may perform learning (e.g., convolutional neural network (CNN) based learning) by using the obtained medical images as learning data. In this case, the computer may segment the brain into the plurality of regions based on the layer structure of the brain and may perform learning on the learning data such that each of the plurality of regions thus segmented is labeled. The computer may create the learning model by performing learning on the learning data. That is, the computer may perform learning based on the learning data and may in advance build (or create) the learning model labeling the brain for each region based on the layer structure of the brain. Accordingly, the computer may input a head image of a specific object as an input value to the learning model and may obtain an output value, in which the head image of the specific object is segmented into a plurality of regions, from the learning model. In this case, the plurality of regions thus output may respectively correspond to brain regions labeled based on the layer structure of the brain.

FIGS. 2A to 7 illustrate examples in which the brain is segmented based on a brain structure and labeling is made for each region, according to an embodiment of the present invention.

As described above, the brain structure may have a layer structure in which layers are arranged in the order of the scalp, the skull, the cerebrospinal fluid, and the inner brain region (i.e., the gray matter/white matter of the cerebrum, the gray matter/white matter of the cerebellum, and the ventricle). Accordingly, as illustrated in FIGS. 2A to 7, the computer may segment a brain into a plurality of brain regions based on a layer arrangement structure of a brain and may apply a label value (i.e., an identification value) to each brain region so as to be labeled.

In an embodiment, the computer may subdivide the inner brain region into cerebrum, cerebellum, and ventricle regions and may apply a specific label value to each subdivided region.

Figure 2A:
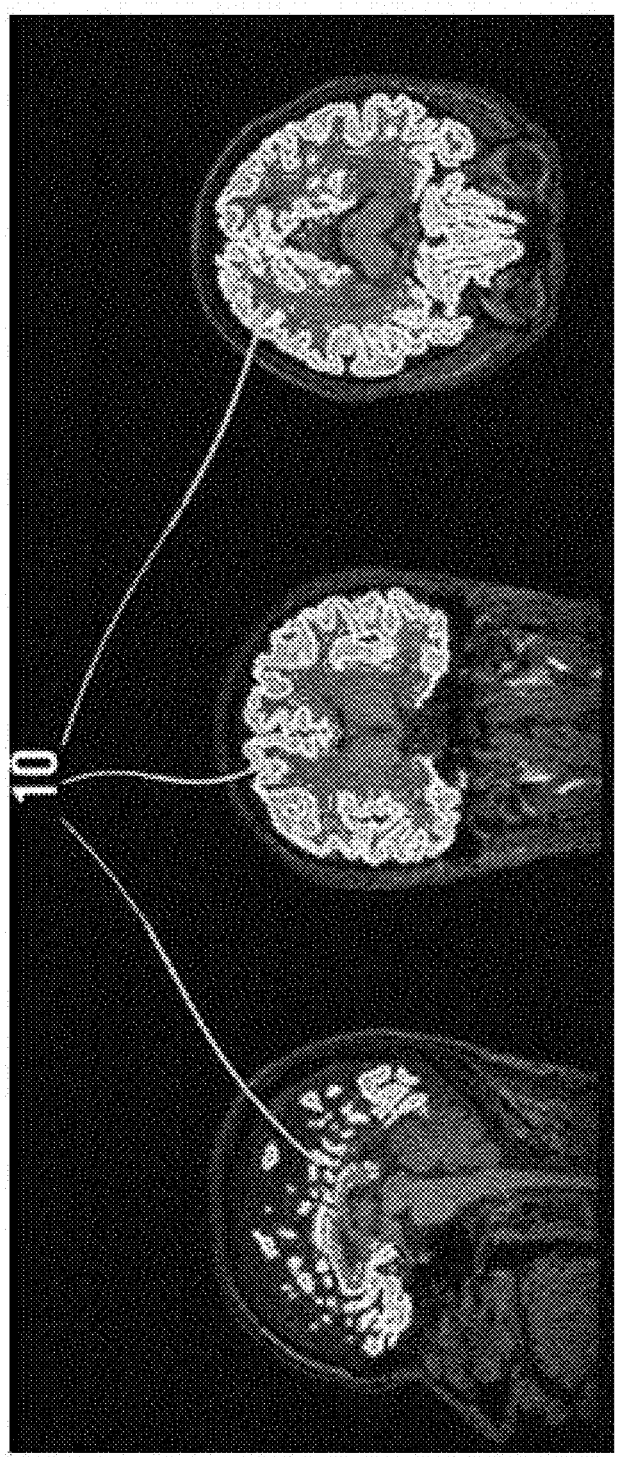
FIGS. 2A to 7 illustrate examples in which a brain is segmented based on a brain structure and labeling is made for each region, according to an embodiment of the present invention.
Figure 2B:
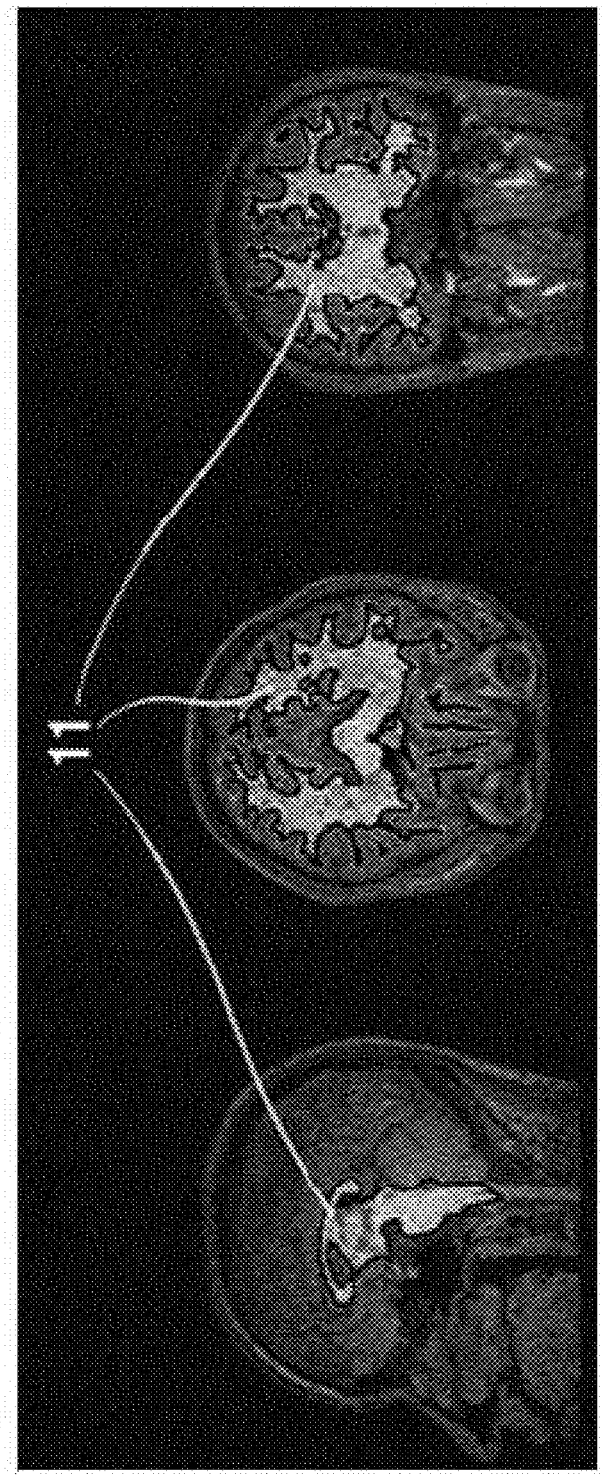

FIG. 2A illustrates a region 10 corresponding to a cerebral gray matter in a head image including the brain, and FIG. 2B illustrates a region 11 corresponding to a cerebral white matter. For example, the computer may set a label value of "1" to the cerebral gray matter region 10 being an outer region of the brain and may set a label value of "0" to the cerebral white matter region 11 being an inner region of the brain.

Figure 3A:
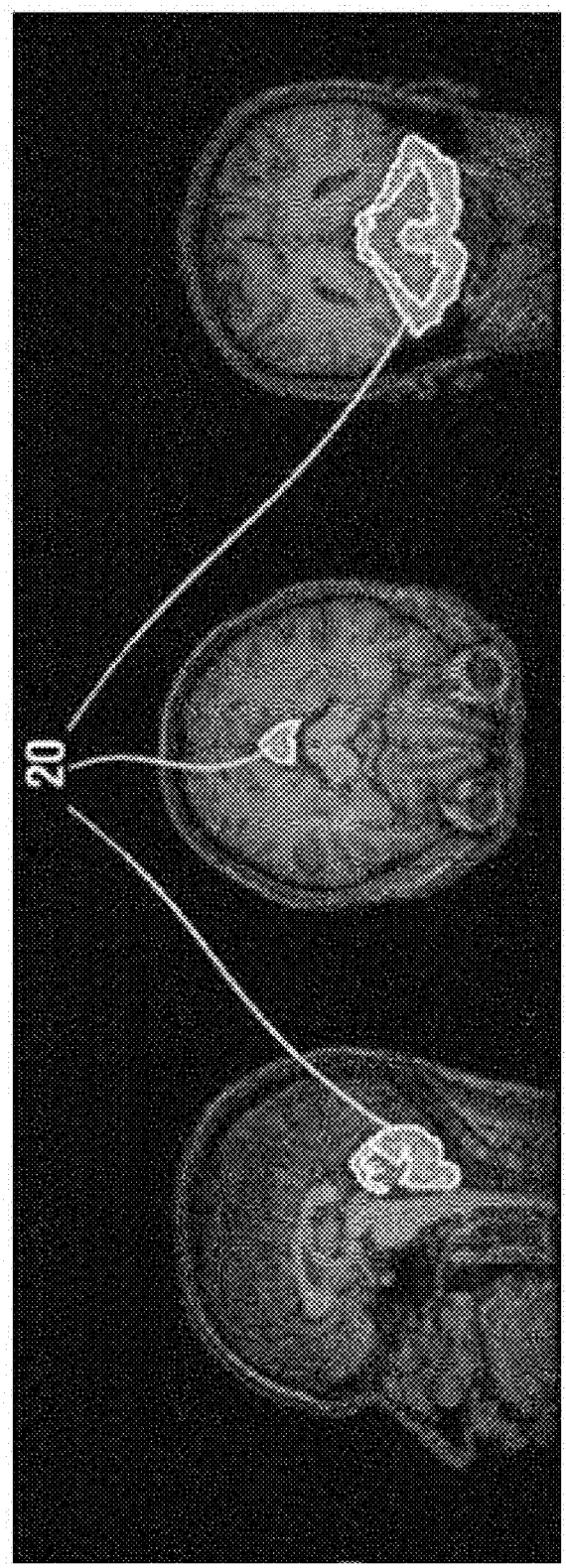
Figure 3B:
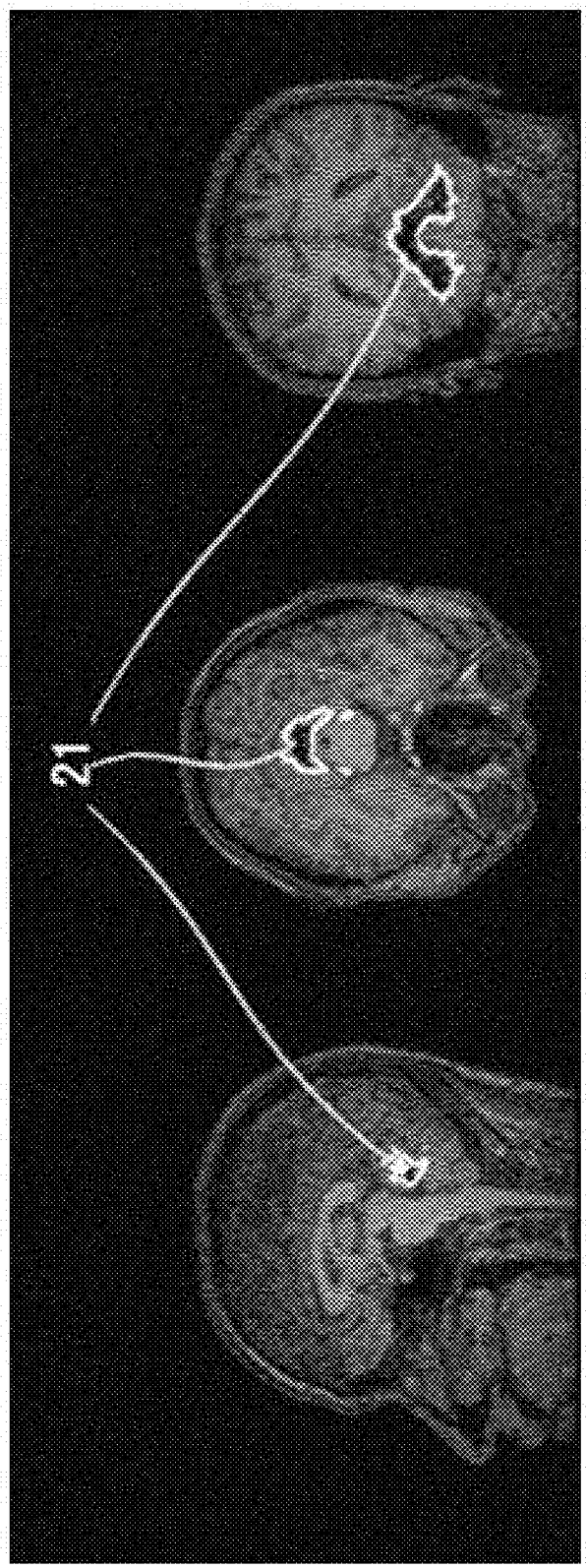

FIG. 3A illustrates a region 20 corresponding to the cerebellar gray matter in the head image including the brain, and FIG. 3B illustrates a region 21 corresponding to the cerebellar white matter. For example, the computer may set a label value of "3" to the cerebellar gray matter region 20 being an outer region of the cerebellum and may set a label value of "4" to the cerebellar white matter region 21 filling an inner region of the cerebellum.

Figure 4:
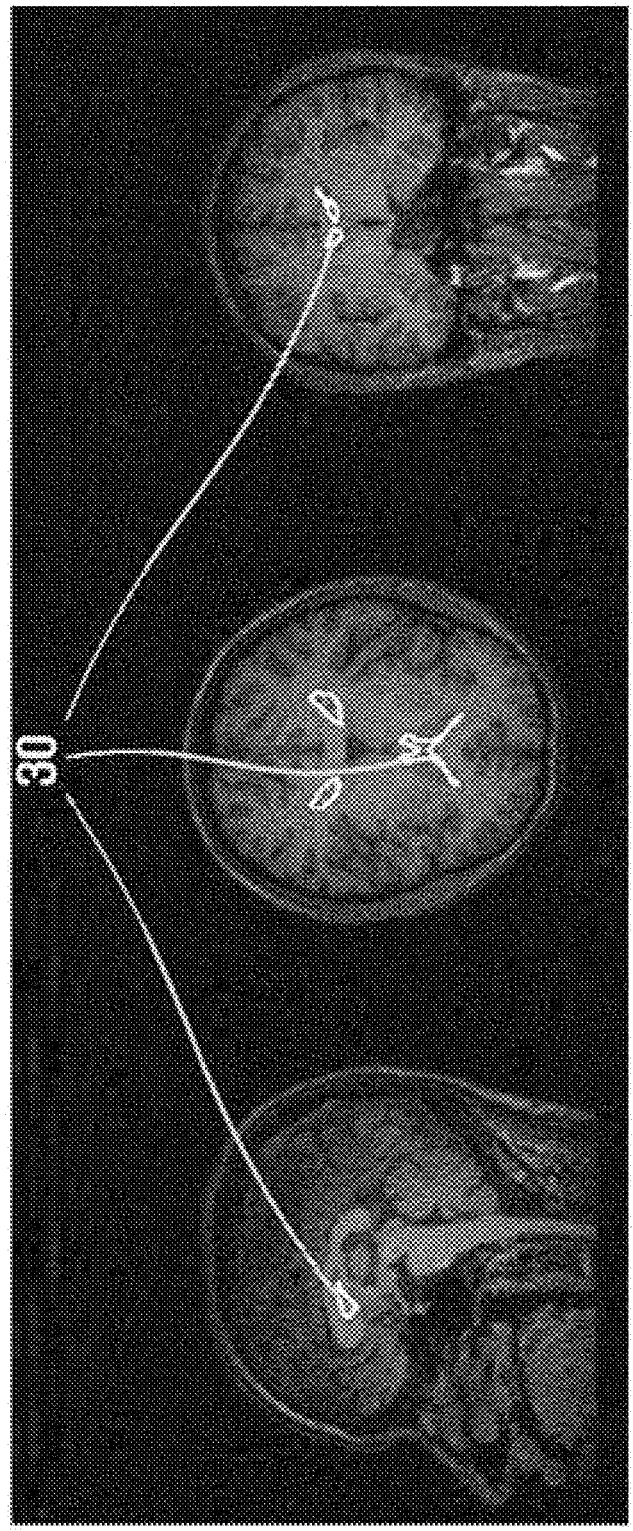

FIG. 4 illustrates a region 30 corresponding to ventricles (or lateral ventricles) in the head image including the brain. For example, the computer may set a label value of "5" to the ventricle region 30 corresponding to empty spaces interconnected in the inner brain region.

Figure 5:
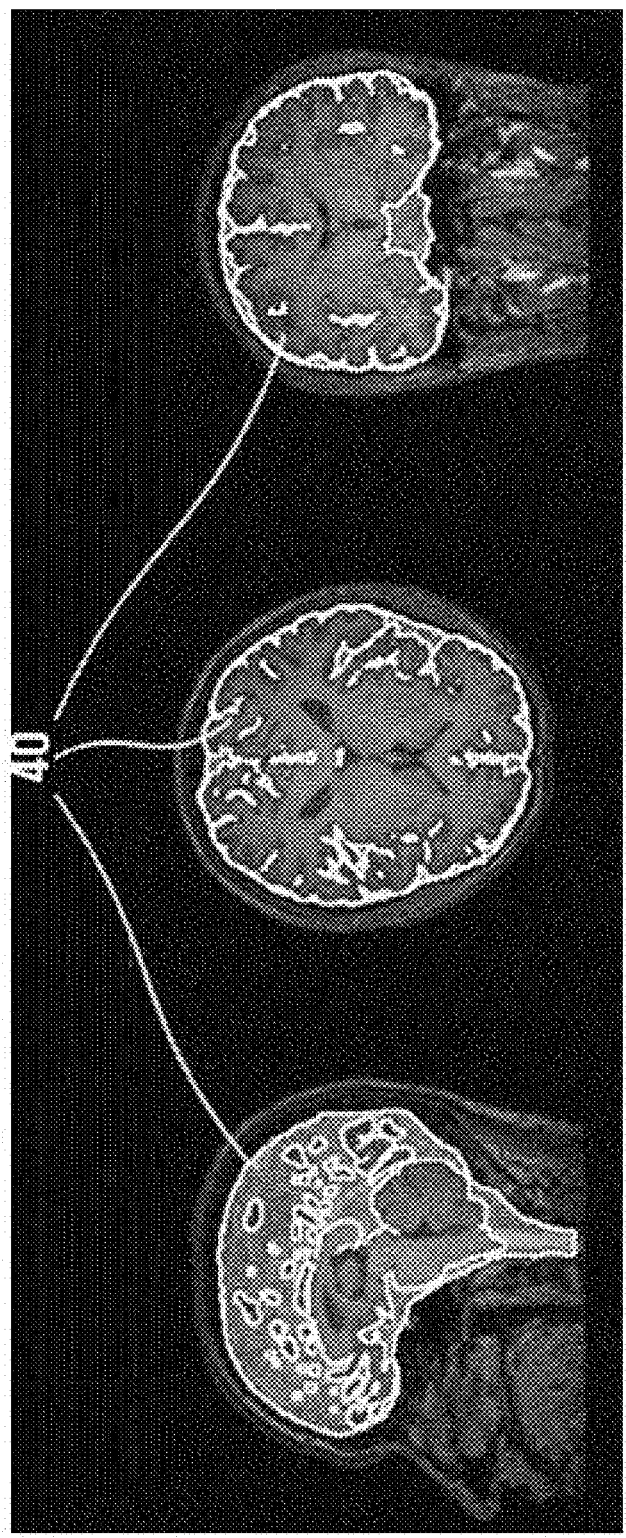

FIG. 5 illustrates a region 40 corresponding to cerebrospinal fluid (CSF) in the head image including the brain. Here, the cerebrospinal fluid 40 refers to a fluid that is filled between the outer portions of the cerebral/cerebellar gray matters and the skull. In an embodiment, the region 40 corresponding to the cerebrospinal fluid may include a superior saggitalsinus and a transverse sinus. Also, a falx may be classified as a portion of the cerebrospinal fluid. For example, the computer may set a label value of "6" to the cerebrospinal fluid region 40.

Figure 6:
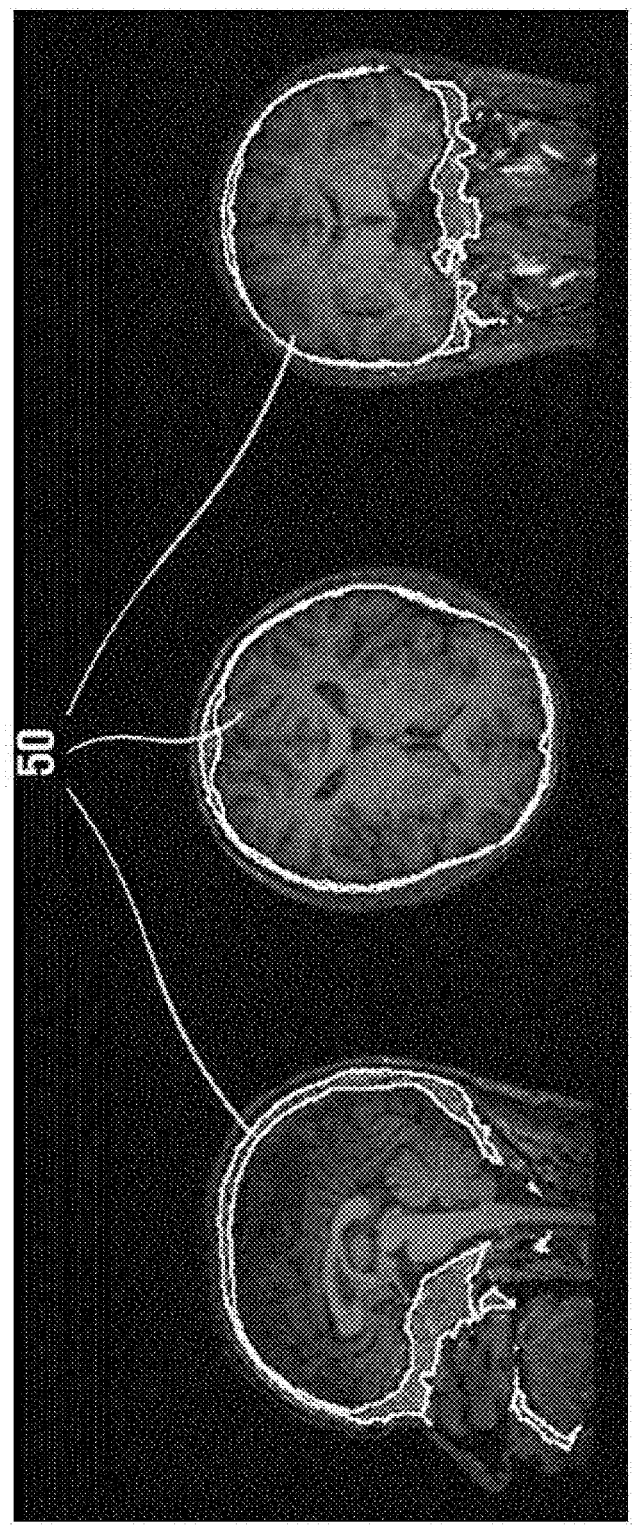

FIG. 6 illustrates a region 50 corresponding to a skull in the head image including the brain. For example, the computer may set a label value of "7" to the skull region 50.

Figure 7:
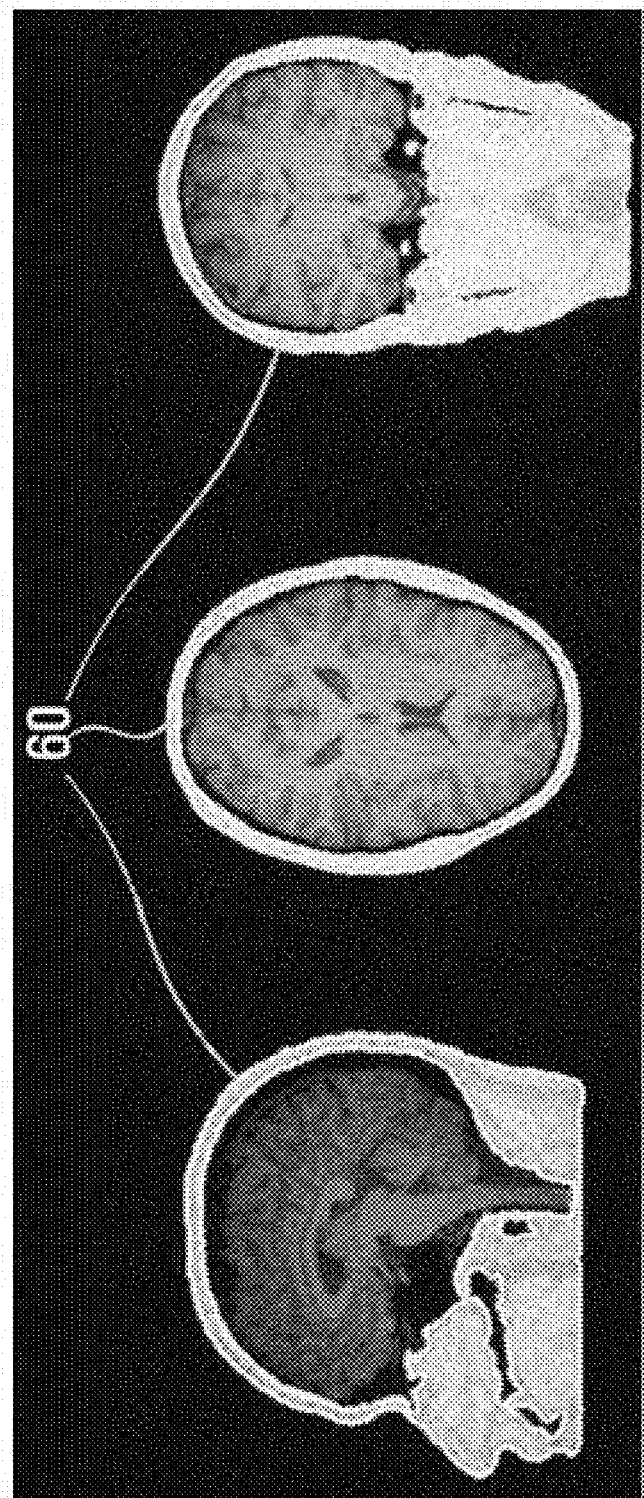

FIG. 7 illustrates a region 60 corresponding to a skin in the head image including the brain. For example, the computer may set a label value of "8" to the skin region 60.

As illustrated in FIGS. 2A to 7, the computer may segment a head image into eight brain regions respectively labeled with the label values of "1" to "8" based on the brain structure. Here, the segmentation into the eight brain regions may be based on a clinical layer structure. Accordingly, the computer may segment the head image of the specific object obtained in step 100 to a plurality of regions so as to correspond to brain regions having given label values.

In this case, as described above, the computer may create the learning model, in which a head image is segmented into eight brain regions labeled with the label values of "1" to "8", as illustrated in FIGS. 2A to 7, through the learning using the deep learning. In this case, the computer may input the head image of the specific object obtained in step S100 to the learning model and thus may obtain the head image that is segmented into the eight brain regions labeled with the label values of "1" to Returning to FIG. 1, the computer performs correction on the plurality of regions segmented in step S200, by using the layer arrangement condition of the brain (S300).

In an embodiment, the computer may determine whether the head image segmented into the plurality of regions coincides with the layer arrangement condition of the brain, may extract a region, which does not coincide with the layer arrangement condition of the brain, from among the plurality of regions, and may perform correction on the extracted region.

Here, as described above, the layer arrangement condition of the brain may be a condition that is set based on the layer structure of the brain in which a brain layer is arranged in the order of the skin, the skull, the cerebrospinal fluid, and the inner brain region (i.e., the gray matter/white matter of the cerebrum, the gray matter/white matter of the cerebellum, and the ventricle). For example, as illustrated in FIGS. 2A to 7, the computer may set the condition so as to have an arrangement relationship coinciding with the brain layer structure segmented into the eight brain regions labeled with the label values of "1" to "8".

In an embodiment, the layer arrangement condition of the brain may include at least one of first to fifth conditions to be described below.

According to the first condition, a layer disposed outside a layer corresponding to the skin should not exist. For example, a region having any label value cannot be disposed outside the region corresponding to the label value of "8" (i.e., the skin of FIG. 7).

According to the second condition, a layer corresponding to the cerebrospinal fluid should not contact the layer corresponding to the skin. For example, the region corresponding to the label value of "6" (i.e., the cerebrospinal fluid of FIG. 5) should be disposed not to be in direct contact with the region corresponding to the label value of "8" (i.e., the skin of FIG. 7).

According to the third condition, a layer corresponding to the inner brain region should not contact the layer corresponding to the skull or the layer corresponding to the skin. For example, the regions corresponding to the label values of "1" to "5" (i.e., the cerebrum of FIGS. 2A and 2B, the cerebellum of FIGS. 3A and 3B, and the ventricle of FIG. 4) should be disposed not to be in direct contact with the region corresponding to the label value of "7" (i.e., the skull of FIG. 6) or the label value of "8" (i.e., the skin of FIG. 7).

According to the fourth condition, a layer corresponding to the white matter in the inner brain region should not exist outside the layer corresponding to the gray matter (i.e., cortex) in the inner brain region. For example, the region corresponding to the label value of "2" (i.e., the cerebral white matter in FIG. 2B) should not be disposed outside the region corresponding to the label value of "1" (i.e., the cerebral gray matter in FIG. 2A). Also, the region corresponding to the label value of "4" (i.e., the cerebellar white matter in FIG. 3B) should not be disposed outside the region corresponding to the label value of "3" (i.e., the cerebellar gray matter in FIG. 3A).

According to the fifth condition, an arrangement distribution of all the layers in the layer structure of the brain should be within a given range. For example, a label value, which is not distributed within the given range with all the labels (i.e., the label values of "1" to "8") and is distributed in a region getting out of the given range, should be minimized.

That is, the computer may determine whether the head image segmented into the plurality of regions has the arrangement relationship coinciding with the layer structure of the brain (e.g., the label values illustrated in FIGS. 2A to 7), based on the first to fifth conditions described above. The computer may extract a region, which has an arrangement relationship not coinciding with the layer structure of the brain, from the head image depending on a determination result and may correct the extracted region. For example, when correcting the region not satisfying the layer arrangement condition of the brain, the computer may rearrange the corresponding region so as to coincide with the order of the skin, the skull, the cerebrospinal fluid, and the inner brain region.

FIGS. 8A to 8D are diagrams illustrating examples of results of segmenting a head image into a plurality of regions, according to an embodiment of the present invention. For example, FIGS. 8A to 8D may be result of performing step S200.

As described above, after segmenting a head image of an object into a plurality of brain regions, the computer may determine whether each brain region thus segmented satisfies the layer arrangement condition of the brain (i.e., the first to fifth conditions).

Figure 8B:
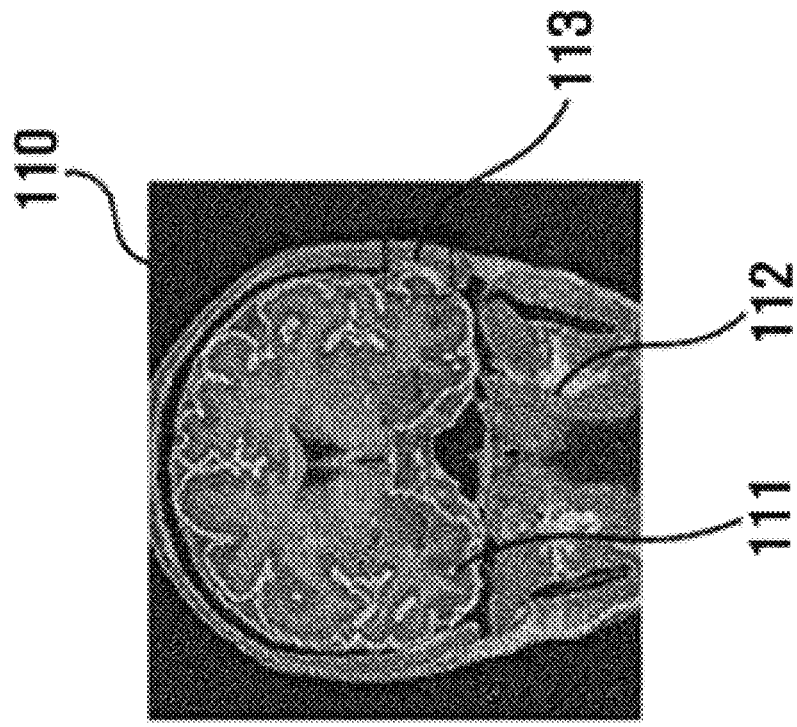
FIGS. 8A to 8D are diagrams illustrating examples of results of segmenting a head image into a plurality of regions, according to an embodiment of the present invention.
Figure 8A:
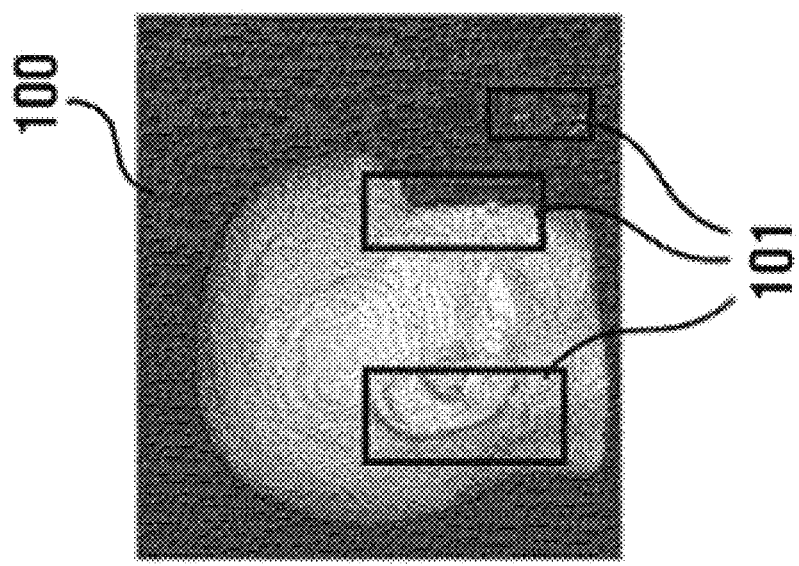

For example, in the case of a head image 100 segmented into a plurality of regions as illustrated in FIG. 8A, the computer may recognize that any other layer (e.g., a skull) 101 is present outside the layer corresponding to the skin, in the head image 100, based on the layer arrangement condition of the brain (i.e., the first to fifth conditions) and thus may determine that the first condition is not satisfied. In this case, the computer may correct the layer region (e.g., a skull) 101 not satisfying the first condition so as to be appropriate to the layer structure of the brain. For example, the computer may correct the head image such that the layer region (e.g., a skull) 101 not satisfying the first condition is disposed in an inner region of the skin.

In this case, in an embodiment, when determining whether to satisfy the first condition, the computer may first obtain a skin layer region including a difference region corresponding to a result of subtracting an original skull region before binary dilation from a region in which the skull is binary dilated. In this case, the skin layer region fully surrounds the skull. Next, the computer may extract a portion, which newly surrounds the skull, of the skin layer region including the difference region and may determine the extracted portion as a "region present outside the skin". In this case, the computer may seize that there is not satisfied the first condition that a layer disposed outside the layer corresponding to the skin should not exist, by extracting the "region present outside the skin" from the head image.

For another example, in the case of a head image 110 segmented into a plurality of regions as illustrated in FIG. 8B, the computer may recognize that a portion 113, at which a partial region of a layer 111 corresponding to the cerebrospinal fluid contacts a partial region of a layer 112 corresponding to the skin, is present in the head image 110, based on the layer arrangement condition of the brain (i.e., the first to fifth conditions) and thus may determine that the second condition is not satisfied. In this case, the computer may correct the contact region 113 not satisfying the second condition so as to be appropriate to the layer structure of the brain. For example, the computer may correct the head image such that the contact portion 113 is disposed in the inner region of the skin.

In this case, in an embodiment, when determining whether to satisfy the second condition, the computer may first obtain a skull layer region including a difference region corresponding to a result of subtracting an original cerebrospinal fluid region before binary dilation from a region in which the cerebrospinal fluid is binary dilated. In this case, the skull layer region fully surrounds the cerebrospinal fluid. Then, the computer may extract a portion, which newly surrounds the cerebrospinal fluid, of the skull layer region including the difference region and may determine the extracted portion as a "region in which the cerebrospinal fluid is in direct contact with the skin". In this case, the computer may seize that there is not satisfied the second condition that a layer corresponding to the cerebrospinal fluid should not contact the layer corresponding to the skin, by extracting the "region in which the cerebrospinal fluid is in direct contact with the skin" from the head image.

For another example, in the case of recognizing that a portion at which the layer corresponding to the inner brain region (e.g., brain regions corresponding to the label values of "1" to "5") contacts a portion of the skull and/or the skin is present in the head image, based on the layer arrangement condition of the brain (i.e., the first to fifth conditions), the computer may determine that the third condition is not satisfied. In this case, the computer may correct the contact portion not satisfying the third condition so as to be appropriate to the layer structure of the brain. For example, the computer may correct the head image such that a contact portion is disposed within the skull and/or the skin.

In this case, in an embodiment, when determining whether to satisfy the third condition, the computer may first obtain a cerebrospinal fluid layer region including a difference region corresponding to a result of subtracting an original inner brain region before binary dilation from a region in which the whole of the inner brain region (i.e., the cerebrum, the cerebellum, and the ventricle) is binary dilated. In this case, the cerebrospinal fluid layer region fully surrounds the inner brain region. Afterwards, the computer may extract a portion, which newly surrounds the inner brain region, of the cerebrospinal fluid layer region including the difference region and may determine the extracted portion as a "region at which the inner brain region is in direct contact with the skull and/or the skin". In this case, the computer may seize that there is not satisfied the third condition that the layer corresponding to the inner brain region should not contact the layer corresponding to the skull or the skin, by extracting the "region at which the inner brain region is in direct contact with the skull and/or the skin" from the head image.

Figure 8C:
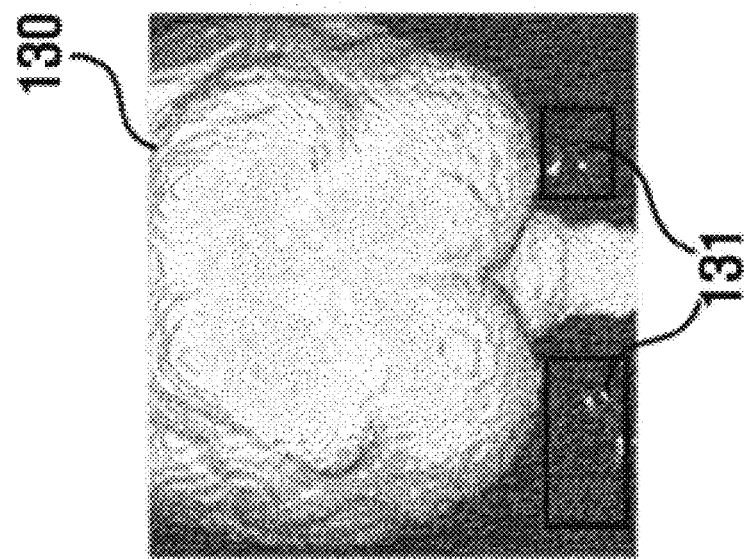

For another example, in the case of a head image 120 segmented into a plurality of regions as illustrated in FIG. 8C, the computer may recognize that a partial region 121 of the layer corresponding to the cerebral white matter is present outside the layer corresponding to the cerebral gray matter, in the head image 120, based on the layer arrangement condition of the brain (i.e., the first to fifth conditions) and thus may determine that the fourth condition is not satisfied. In this case, the computer may correct the partial region 121 not satisfying the fourth condition so as to be appropriate to the layer structure of the brain. For example, the computer may correct the head image such that the partial region 121 not satisfying the fourth condition is disposed within the cerebral gray matter.

In this case, in an embodiment, when determining whether to satisfy the fourth condition, the computer may first obtain a first difference region corresponding to a result of subtracting an original white matter region before binary dilation from a region in which the white matter is binary dilated and may obtain a second difference region corresponding to a result of subtracting an original gray matter region before binary dilation from a region in which the gray matter is binary dilated. Next, the computer may extract a common portion (i.e., an intersection portion) of the first difference region and the second difference region and may determine the extracted common portion as a "portion at which the gray matter does not surround the white matter". In this case, the computer may seize that there is not satisfied the fourth condition that the layer corresponding to the white matter in the inner brain region should not exist outside the layer corresponding to the gray matter (i.e., cortex) in the inner brain region, by extracting the "portion at which the gray matter does not surround the white matter" from the head image.

Figure 8D:
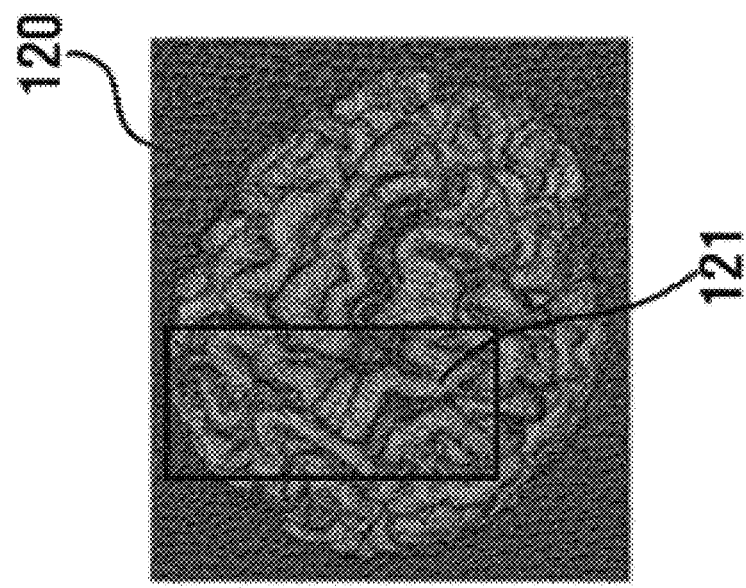

For another example, in the case of a head image 130 segmented into a plurality of regions as illustrated in FIG. 8D, the computer may recognize that a portion 131, which is not distributed in a lump together with all the brain regions and is distributed at a location getting out of a given range, is present in the head image 130, based on the layer arrangement condition of the brain (i.e., the first to fifth conditions) and thus may determine that the fifth condition is not satisfied. In this case, the computer may correct the portion 131 not satisfying the fifth condition so as to be appropriate to the layer structure of the brain. For example, the computer may perform a connected component-based noise rejection operation to correct the portion 131 not satisfying the fifth condition.

In this case, in an embodiment, when determining whether to satisfy the fifth condition, the computer may perform an operation (hereinafter referred to as a "binary fill hole operation"), which is performed to fill a hole, on the remaining layer region except for the ventricle and may then perform the connected component-based noise rejection operation to extract a region, which is formed of the largest lump, from among all the brain regions. In this case, the computer may determine regions, which are removed through the connected component-based noise rejection operation, from among all the brain regions as a "portion that is not distributed within a given range with all the brain regions". Here, with regard to the ventricle region, in the case where there is a ventricle region whose size does not reach a reference size (e.g., 30% of the size of the largest lump), the computer may determine the corresponding ventricle region as a "portion that is not distributed within a given range with all the brain regions", based on the size of the region formed of the largest lump.

Here, because the binary fill hole operation is performed on all the brain regions except for the ventricle when determining whether to satisfy the fifth condition, the inside of each brain region may be filled. For this reason, the rearrangement may be required to correspond to the layer order of the brain. In this case, the computer may first rearrange each brain region so as to correspond to the layer order of the brain (e.g., the order of the skin, the skull, the cerebrospinal fluid, and the inner brain region), and may determine whether a region not satisfying the fifth condition still exists, for each of the rearranged brain regions, through the connected component-based noise rejection operation. Afterwards, the computer may set an N×N×N-sized cube region with respect to a region that still does not satisfy the fifth condition and may check a layer (e.g., a label value) to which surrounding regions of the set cube region belong. The computer may select a layer (e.g., a label value), to which a largest number of surrounding regions belong, depending on a check result and may correct the region not satisfying the fifth condition so as to belong to a region of the selected layer.

As described above, after segmenting a head image of an object into a plurality of brain regions, the computer may determine whether each brain region thus segmented satisfies the layer arrangement condition of the brain (i.e., the first to fifth conditions).

In this case, the computer may determine whether to have an arrangement relationship coinciding with the layer structure of the brain in the order of the fifth condition, the fourth condition, the third condition, the second condition, the first condition, and then the fifth condition.

In an embodiment, first, the computer may determine whether a portion, which is not distributed in a lump together with all the brain regions and is distributed at a location getting out of a given range, is present in the head image segmented into the plurality of regions. That is, the computer may detect a brain region that is remote from all the brain regions. This corresponds to the process of filling a hole of each layer (e.g., regions that are segmented for respective brain regions based on the brain structure and are specified to the label values of "1" to "8") through the binary fill hole operation and extracting only a region formed of the largest lump except for the ventricle through the connected component label technique (i.e., the connected component-based noise rejection operation), in the process of determining whether to coincide with the fifth condition.

Through the above process, the head image segmented into the plurality of regions may be in a state where the hole is filled and may then be processed in a state where a brain region remote from all the brain regions is removed. Accordingly, the computer may perform the following process by using the head image processed as described above.

The computer may determine whether the head image, which experiences the binary fill hole operation and the connected component-based noise rejection operation described above, satisfies the fourth condition that the layer corresponding to the cerebral white matter should not exist outside the layer corresponding to the cerebral gray matter. The process of determining whether to satisfy the fourth condition is described in detail with reference to FIGS. 8A to 8D, and thus, additional description will be omitted to avoid redundancy. The computer may detect whether there is a "portion at which the gray matter does not surround the white matter", from the head image as a result of determining the fourth condition and may correct the detected portion.

Next, the computer may determine whether the head image, which experiences the binary fill hole operation and the connected component-based noise rejection operation described above, satisfies the third condition that the layer corresponding to the inner brain region (i.e., the cerebrum, the cerebellum, and the ventricle) should not contact the layer corresponding to the skull and/or the skin. The process of determining whether to satisfy the third condition is described in detail with reference to FIGS. 8A to 8D, and thus, additional description will be omitted to avoid redundancy. As a result of determining the third condition, the computer may detect whether there is a "portion at which the inner brain region is in direct contact with the skull and/or the skin" and may correct the detected portion.

Next, the computer may determine whether the head image, which experiences the binary fill hole operation and the connected component-based noise rejection operation described above, satisfies the second condition that the layer corresponding to the cerebrospinal fluid should not contact the layer corresponding to the skin. The process of determining whether to satisfy the second condition is described in detail with reference to FIGS. 8A to 8D, and thus, additional description will be omitted to avoid redundancy. As a result of determining the second condition, the computer may detect whether there is a "portion at which the cerebrospinal fluid is in direct contact with the skin" and may correct the detected portion.

Afterwards, the computer may determine whether the head image, which experiences the binary fill hole operation and the connected component-based noise rejection operation described above, satisfies the first condition that any other layer disposed outside the layer corresponding to the skin should not exist. The process of determining whether to satisfy the first condition is described in detail with reference to FIGS. 8A to 8D, and thus, additional description will be omitted to avoid redundancy. As a result of determining the first condition, the computer may detect whether "any other region, not the skin, is present outside the skin" and may correct the detected region.

Next, the computer may rearrange each layer region processed in the order of the above process, that is, the fourth condition, the third condition, the second condition, and the first condition, so as to correspond to the brain structure. In this case, because the inside of each layer region experiencing the above process is filled through the binary fill hole operation, it is necessary to rearrange each layer so as to correspond to the brain structure. Accordingly, the computer may rearrange each layer in the order of the skin, the skull, the cerebrospinal fluid, and the inner brain region.

After the rearrangement of each layer, the computer may check whether a region remote from all the brain regions is present, with respect to each layer thus rearranged. In this case, the computer may apply the connected component label technique to each layer thus rearranged. Afterwards, when a region remote from all the brain regions exists, the computer may set a cube region of size N×N×N and may extract surrounding regions of the cube region thus set. In this case, the computer may check a layer (e.g., a label value) to which the surrounding regions extracted from the cube region belong and thus may detect a layer that is most distributed around the corresponding cube. Accordingly, the computer may perform correction such that the region (i.e., the corresponding cube region) remote from all the brain regions is changed to a layer region that is most distributed around the region.

That is, the computer may determine whether a head image has an arrangement relationship coinciding with the layer structure of the brain in the order of the fifth condition, the fourth condition, the third condition, the second condition, the first condition, and then the fifth condition, which is described above, and may perform correction on a layer not coinciding with the layer structure of the brain. As a result, the computer may obtain the brain image coinciding with the clinical brain structure.

According to the description given with reference to FIGS. 1 to 8D, the computer may obtain a head image corrected by using the layer arrangement condition of the brain. Accordingly, it may be possible to obtain a head image segmented into a plurality of brain regions more accurately.

Also, according to an embodiment of the present invention, the computer may perform three-dimensional brain modeling on an object based on the corrected head image and thus may generate a three-dimensional brain image of the object. In this case, a three-dimensional brain model that coincides with the clinical layer structure of the brain more accurately may be obtained.

Also, according to an embodiment of the present invention, the computer may simulate electrical stimulation for the brain of the object based on the corrected head image. Alternatively, the computer may simulate electrical stimulation for the brain of the object by using the three-dimensional brain image generated based on the corrected head image.

Without using the head image in which each brain region is corrected to coincide with the layer structure of the brain like an embodiment of the present invention, in the case of performing brain modeling by using a general head image (i.e., a head image segmented into incorrect regions) or simulating a transfer process of electrical stimulation for the brain by using the general head image, the electrical stimulation may be applied to an incorrectly segmented brain portion, thereby causing an excessive increase or decrease of an electric field value or the like. That is, in simulating a path through which specific electrical stimulation is propagated in the brain of the object in a state where the specific electrical stimulation is applied to one point of the head of the object, it is impossible to obtain an accurate simulation result.

However, according to an embodiment of the present invention, because there is used a head image in which each brain region is corrected to coincide with the layer structure of the brain, a specific point to which electrical stimulation is to be applied may be specified more accurately in the head image of the object. Accordingly, the accuracy of the simulation result may also be improved.

Figure 9:
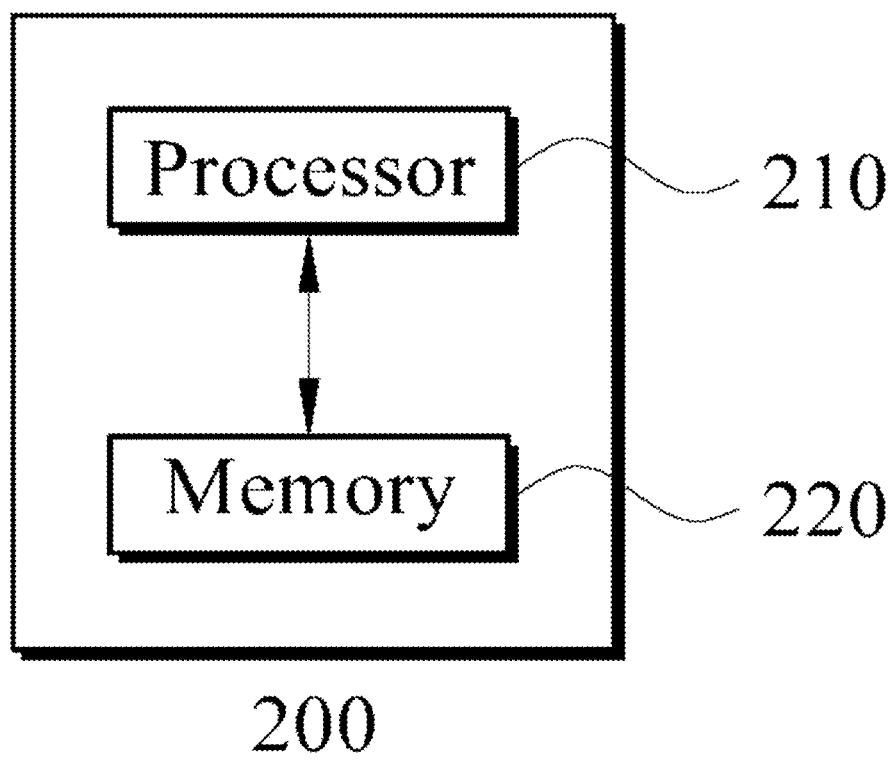
FIG. 9 is a diagram illustrating a configuration of a device which performs a method for correcting a brain image by using a brain structure, according to an embodiment of the present invention.

FIG. 9 is a diagram illustrating a configuration of a device 200 that performs a method for correcting a brain image by using a brain structure, according to an embodiment of the present invention.

Referring to FIG. 9, a processor 210 may include one or more cores (not illustrated) and a connecting path (e.g., a bus or the like) that transmits/receives signals to/from a graphic processing unit (not illustrated) and/or any other component.

The processor 210 according to an embodiment performs the brain image correcting method using the brain structure, which is described with reference to FIGS. 1 to 8D, by executing one or more instructions stored in a memory 220.

For example, by executing the one or more instructions stored in the memory 220, the processor 210 may perform obtaining a head image including a brain of an object, segmenting the head image into a plurality of regions based on a brain structure, and performing a correction on the plurality of regions by using a layer arrangement condition of the brain.

Meanwhile, the processor 210 may further include a random access memory (RAM) (not illustrated) and a read-only memory (ROM) (not illustrated) that temporarily and/or permanently stores signals (or data) processed in the processor 210. Also, the processor 210 may be implemented in the form of a system on chip including at least one of a graphic processing unit, a RAM, and a ROM.

The memory 220 may store programs (i.e., one or more instructions) for processing and control of the processor 210. The programs stored in the memory 220 may be classified into a plurality of modules, based on functions.

According to an embodiment of the present invention, the brain image correcting method using the brain structure, which is described above, may be implemented by a program (or an application) and may be stored in a medium such that the program is executed in combination with a computer being hardware.

For the computer to read the program and to execute the method implemented by the program, the program may include a code that is coded in a computer language, which a processor (e.g., a central processing unit CPU) of the computer may read through a device interface of the computer, such as C, C++, JAVA, or a machine language. The code may include a functional code related to a function that defines necessary functions executing the method, and the functions may include an execution procedure related control code necessary for the processor of the computer to execute the functions in its procedures. Further, the code may further include additional information that is necessary for the processor of the computer to execute the functions or a memory reference related code on which location (address) of an internal or external memory of the computer should be referenced by the media. Further, when the processor of the computer is required to perform communication with another computer or a server in a remote site to allow the processor of the computer to execute the functions, the code may further include a communication related code on how the processor of the computer executes communication with another computer or the server or which information or medium should be transmitted/received during communication by using a communication module of the computer.

The stored medium refers not to a medium, such as a register, a cache, or a memory, which stores data for a short time but to a medium that stores data semi-permanently and is read by a device. In detail, for example, the stored medium may include a read only memory (ROM), a random access memory (RAM), a CD-ROM, a magnetic tape, a floppy disk, and an optical data storage device, but the present invention is not limited thereto. That is, the program may be stored in various recording media on various servers, which the computer may access, or in various recording media on the computer of the user. Further, the media may be distributed in computer systems connected over a network such that codes readable by the computer are stored in a distributed manner.

Steps or operations of the method or algorithm described with regard to an embodiment of the present invention may be implemented directly in hardware, may be implemented with a software module executable by hardware, or may be implemented by a combination thereof. The software module may reside in a random access memory (RAM), a read only memory (ROM), an erasable programmable ROM (EPROM), an electrically erasable programmable ROM (EEPROM), a flash memory, a hard disk, a removable disk, a CD-ROM, or a computer-readable recording medium well known in the art to which the present invention pertains.

According to the present invention, a brain image segmented into more accurate brain regions may be generated by segmenting a brain for each region so as to correspond to a layer arrangement condition of the brain and performing correction for each of the brain regions thus segmented.

According to the present invention, a brain image in which brain regions are classified to correspond to a more real brain structure may be obtained by segmenting the brain for each region by using the layer arrangement condition of the brain.

According to the present invention, as there is obtained a brain image in which each brain region is corrected to coincide with a layer structure of the brain, there may be obtained a more accurate target point to which electrical stimulation is to be applied in electrical brain stimulation that is performed to treat various brain diseases. Also, a treatment effect may be improved by obtaining the accurate electrical stimulation point.

According to the present invention, in segmenting each brain region to correspond to the layer structure of the brain, each brain region may be effectively classified in a brain image by using a learning model.

Effects of the present invention are not limited to the effects mentioned above, and other effects not mentioned will be clearly understood by those skilled in the art from the detailed description.

Although an embodiment of the present invention are described with reference to the accompanying drawings, it will be understood by those skilled in the art to which the present invention pertains that the present invention can be carried out in other detailed forms without changing the scope and spirit or the essential features of the present invention. Therefore, the embodiments described above are provided by way of example in all aspects, and should be construed not to be restrictive.

What is claimed is:

1. A method for correcting a brain image by using a brain structure, which is performed by a device, the method comprising:

obtaining a head image including a brain of an object;

segmenting the head image into a plurality of regions based on the brain structure; and performing correction on the plurality of regions by using a layer arrangement condition of a brain, wherein the layer arrangement condition comprises:

a first condition that a layer disposed outside a layer corresponding to a skin does not exist;

a second condition that a layer corresponding to a cerebrospinal fluid does not contact the layer corresponding to the skin;

a third condition that a layer corresponding to an inner brain region does not contact a layer corresponding to a skull or the layer corresponding to the skin;

a fourth condition that a layer corresponding to a white matter in the inner brain region does not exist outside a layer corresponding to a gray matter in the inner brain region; and a fifth condition that an arrangement distribution of all layers in the layer structure of the brain is within a given range, and wherein the performing of the correction comprises:

determining whether the plurality of regions comply with the layer arrangement condition in the order of the fifth condition, the fourth condition, the third condition, the second condition, the first condition, and the fifth condition;

extracting a region, which does not comply with the layer arrangement condition, from among the plurality of regions; and correcting the extracted region to comply with the layer arrangement condition.

2. The method of claim 1, wherein the segmenting into the plurality of regions includes:

segmenting the brain in the head image into the plurality of regions by using a learning model labeling a brain based on the brain structure.

3. The method of claim 2, wherein each of the plurality of regions corresponds to each of brain regions labeled through the learning model through the brain structure.

4. The method of claim 1, wherein the correcting comprises:

rearranging the extracted region so as to comply with the layer structure of the brain arranged in the order of the skin, the skull, the cerebrospinal fluid, and the inner brain region.

5. The method of claim 1, further comprising:

performing three-dimensional brain modeling on the object based on the head image corrected by using the layer arrangement condition of the brain.

6. The method of claim 1, further comprising:

simulating electrical stimulation for the brain of the object based on the head image corrected by using the layer arrangement condition of the brain.

7. A non-transitory recording medium readable by a computer and storing a computer program allowing the computer to perform the brain image correcting method using the brain structure according to claim 1.

8. A device for correcting a brain image by using a brain structure, the device comprising:

a memory configured to store at least one instruction for correcting the brain image by using the brain structure; and a processor configured to execute the at least one instruction stored in the memory, wherein, when the at least one instruction is executed, as a response to the instruction, the processor is configured to:

obtain a head image including a brain of an object;

segment the head image into a plurality of regions based on the brain structure; and perform correction on the plurality of regions by using a layer arrangement condition of a brain, wherein the layer arrangement condition comprises:

a first condition that a layer disposed outside a layer corresponding to a skin does not exist;

a second condition that a layer corresponding to a cerebrospinal fluid does not contact the layer corresponding to the skin;

a third condition that a layer corresponding to an inner brain region does not contact a layer corresponding to a skull or the layer corresponding to the skin;

a fourth condition that a layer corresponding to a white matter in the inner brain region does not exist outside a layer corresponding to a gray matter in the inner brain region; and a fifth condition that an arrangement distribution of all layers in the layer structure of the brain is within a given range, and wherein the processor is further configured to:

determine whether the plurality of regions comply with the layer arrangement condition in the order of the fifth condition, the fourth condition, the third condition, the second condition, the first condition, and the fifth condition;

extract a region, which does not comply with the layer arrangement condition, from among the plurality of regions; and correct the extracted region to comply with the layer arrangement condition.

9. The device of claim 8, wherein, when segmenting the head image into the plurality of regions, the processor is further configured to segment the brain in the head image into the plurality of regions by using a learning model labeling a brain based on the brain structure.

10. The device of claim 8, wherein, when the processor corrects the extracted region, the processor is further configured to rearrange the extracted region so as to comply with the order of the skin, the skull, the cerebrospinal fluid, and the inner brain region.

11. The device of claim 8, wherein the processor is further configured to simulate electrical stimulation for the brain of the object based on the head image corrected by using the layer arrangement condition of the brain.

* * * * *